(12) United States Patent
Yanuma

(10) Patent No.: US 9,345,539 B2
(45) Date of Patent: May 24, 2016

(54) TREATMENT DEVICE

(75) Inventor: Yutaka Yanuma, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1243 days.

(21) Appl. No.: 11/840,596

(22) Filed: Aug. 17, 2007

(65) Prior Publication Data
US 2009/0048487 A1 Feb. 19, 2009

(51) Int. Cl.
A61B 18/14 (2006.01)
A61B 18/00 (2006.01)
A61B 18/18 (2006.01)

(52) U.S. Cl.
CPC ... *A61B 18/1492* (2013.01); *A61B 2018/00601* (2013.01); *A61B 2018/144* (2013.01); *A61B 2018/1407* (2013.01); *A61B 2018/1861* (2013.01)

(58) Field of Classification Search
USPC ............. 606/32–50, 110, 113, 127–128, 167, 606/154, 171; 604/22; 206/363; 600/104–105
See application file for complete search history.

(56) References Cited

U.S. PATENT DOCUMENTS

| | | | | |
|---|---|---|---|---|
| 4,325,374 A | * | 4/1982 | Komiya | 606/47 |
| 4,485,812 A | * | 12/1984 | Harada et al. | 606/47 |
| 5,024,617 A | * | 6/1991 | Karpiel | 606/47 |
| 5,163,938 A | * | 11/1992 | Kambara et al. | 606/47 |
| 5,323,768 A | * | 6/1994 | Saito et al. | 600/106 |
| 5,810,807 A | * | 9/1998 | Ganz et al. | 606/47 |
| 5,863,366 A | * | 1/1999 | Snow | 156/143 |
| 5,967,984 A | * | 10/1999 | Chu et al. | 600/439 |
| 5,984,920 A | * | 11/1999 | Steinbach | 606/47 |
| 6,471,702 B1 | | 10/2002 | Goto | |
| 6,579,300 B2 | * | 6/2003 | Griego | A61B 17/320016 604/167.01 |
| 6,712,817 B1 | * | 3/2004 | Goto et al. | 606/47 |
| 6,827,718 B2 | * | 12/2004 | Hutchins et al. | 606/47 |
| 7,311,703 B2 | * | 12/2007 | Turovskiy et al. | 606/33 |
| 7,585,298 B2 | * | 9/2009 | Kawahara et al. | 606/45 |

(Continued)

FOREIGN PATENT DOCUMENTS

EP 1 688 099 A1 8/2006
JP 4-307055 A 10/1992

(Continued)

OTHER PUBLICATIONS

Notice of Reasons for Rejection dated Dec. 11, 2012 from corresponding Japanese Patent Application No. 2008-201259, together with an English language translation.

*Primary Examiner* — Ronald Hupczey, Jr.
(74) *Attorney, Agent, or Firm* — Scully, Scott, Murphy & Presser, P.C.

(57) ABSTRACT

A treatment device according to the present invention includes: an elongated sheath having flexibility, the sheath being passed through an endoscope and introduced to an object to be treated; an incision knife section disposed approximately along an axial line of the sheath around an outer periphery at the distal end thereof, the incision knife section being used for incising tissue of the object to be treated; and a rotation-torque-transmitting section extending from a proximal end of the elongated sheath maneuvered by an endoscopist to an intermediate section of the incision knife section in the axial line direction, the rotation-torque-transmitting section rotating the sheath by transmitting rotation torque input at the proximal end of the sheath.

13 Claims, 19 Drawing Sheets

(56) References Cited

U.S. PATENT DOCUMENTS 7,648,502 B2 * 1/2010 Jacques ..................... 606/47
2002/0095168 A1   7/2002 Griego et al.
2007/0100337 A1 * 5/2007 Kawahara et al. ............. 606/46

FOREIGN PATENT DOCUMENTS

JP      9-206309 A    8/1997
JP      H9-285472    11/1997

* cited by examiner

TREATMENT DEVICE

BACKGROUND OF THE INVENTION

1. Field of the Invention

The present invention relates to treatment devices for conducting natural orifice treatment to tissue.

2. Background Art

Endoscopic procedures for extracting a calculus from the bile duct may sometimes meet with difficulty in extracting the calculus from a narrow condition of the papilla, that is, the exit of the bile duct. The calculus in this case is extracted by incising spincter muscles around the papilla by using a papillotome passed through an endoscope and expanding the exit of the bile duct. Generally spincter muscles around the papilla are incised in a direction of an encircling fold. The direction of the encircling fold conforms to the direction of the bile duct extending around the papilla and may be subject to less bleeding because relatively few blood vessels existing in this direction.

Inserting an endoscope suitable for pancreatic-and-biliary endoscopy into the duodenum can obtain an image showing the bile duct directed in a twelve-o'clock direction. An endoscope of this type is provided with a raising block that can move the papillotome up and down in the twelve-o'clock direction. Furthermore, a papillotome inserted using the pancreatic-and-biliary endoscopy for incising a teat spinster muscles is manufactured so that a knife portion thereof is automatically directed in the twelve-o'clock direction in an image endoscopically obtained when the papillotome protrudes from the distal end of the endoscope.

The knife portion of the papillotome is stretched for incision. The knife portion separated alone from a sheath is compressed onto the papilla. This provides significant pressure between the knife portion and the incised part of the tissue. Tilting the raising block while supplying electric current to the knife portion causes the distal end of the papillotome to move in the twelve-o'clock direction, thereby incising the papilla.

However, the direction of the bile duct in the vicinity of the papilla may be different from the twelve-o'clock direction in the endoscopically obtained image in some cases including, e.g., variations among individual patients, strictures existing in organs like the duodenum around the bile duct, or surgery in the past.

To address this, an object of conventional papillotomes is to facilitate incision also in non-twelve-o'clock directions while observing an endoscopically obtained image. Papillotomes of this type are provided with a member for transmitting rotation torque produced at a proximate end to the distal end of a knife portion. For example, Japanese Unexamined Patent Application, First Publication No. H9-285472 describes transmitting of rotation torque by using a plate inserted in the vicinity of the center of a sheath. A distal end section of a conductive wire is connected to the plate. Rotating a knife portion that is at the distal end section of the conductive wire causes the direction of the knife portion to be adjusted accordingly.

SUMMARY OF THE INVENTION

A treatment device according to the present invention includes: an elongated sheath having flexibility, the sheath being passed through an endoscope and introduced to an object to be treated; an incision knife section disposed approximately along an axial line of the sheath around an outer periphery at the distal end thereof, the incision knife section being used for incising tissue of the object to be treated; and a rotation-torque-transmitting section extending from the proximal end of the elongated sheath maneuvered by an endoscopist to an intermediate section of the incision knife section in the axial line direction, the rotation-torque-transmitting section rotating the sheath by transmitting rotation torque input at the proximal end of the sheath.

DETAILED DESCRIPTION OF THE INVENTION

The embodiments will be described below. In the embodiments, the same components are designated by the same numerals and duplicate description is omitted.

First Embodiment

Figure 1:
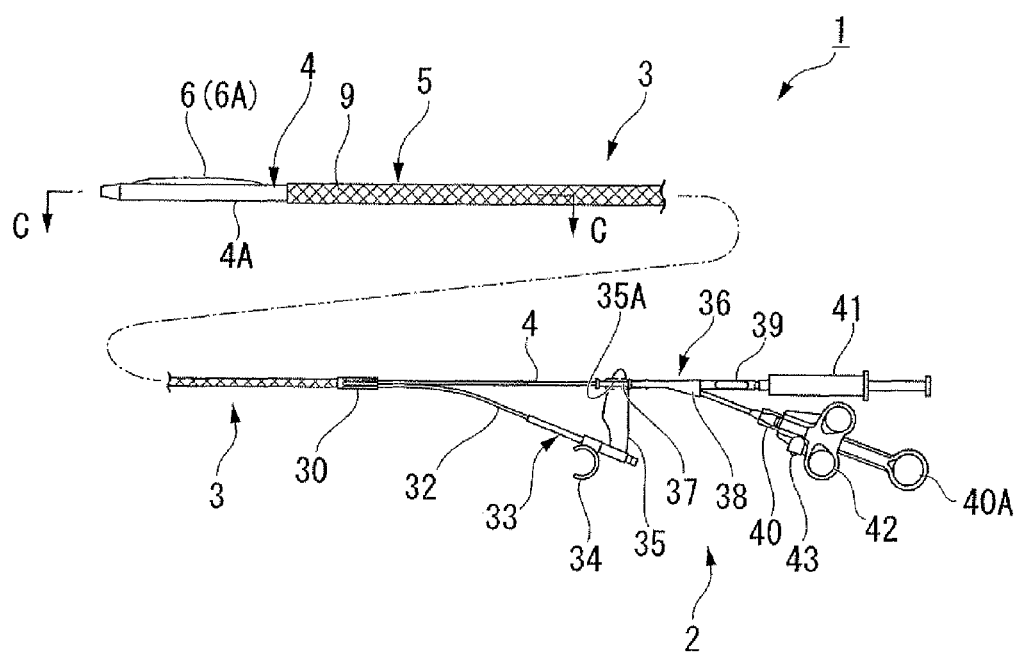
FIG. 1 is a schematic diagram of a papillotome as a treatment device.

FIG. 1 shows a configuration of a papillotome as an example of a treatment device. A papillotome 1 has a long flexible insertion section 3 extended from an operation section 2 that is operated by an operator. The insertion section 3 is provided with a sheath 4 and a first rotation torque-transmitting section 5 that covers the outer periphery of the sheath 4. In addition, a conductive wire 6 for use in incision extends to a side of the distal end of the sheath 4.

Figure 2:
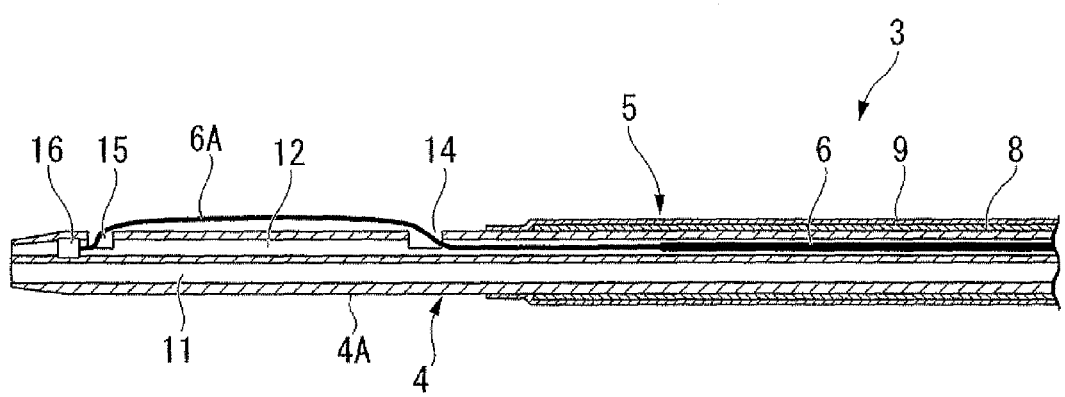
FIG. 2 is a cross-section of a distal end section of the papillotome shown in FIG. 1.
Figure 3:
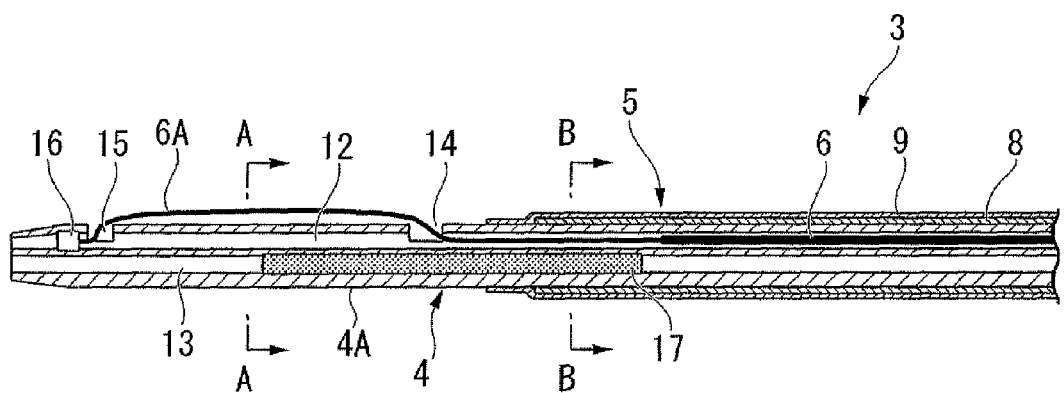
FIG. 3 is a cross-section of a distal end section of the papillotome shown in FIG. 1 viewed differently from FIG. 2.

The outer periphery except for a distal end section 4A is covered with the first rotation torque-transmitting section 5. As illustrated in FIGS. 2 and 3, the first rotation torque-transmitting section 5 is formed by a metal-made blade 8 attached onto the sheath 4 is further covered by an insulative tube 9. Usable examples of the blade 8 include a tubular shape of a plurality of stainless-steel-made wire bundles weaved in a grid form; a stainless-steel wire in a tubular shape or at least a band of stainless-steel bands wound in a coil state; or at least two stainless-steel wires wound in a coil while differentiating winding directions. The distal end section of the sheath 4 may be pre-curved (curled) in order to facilitate insertion into the papilla. Alternatively, the distal end section of the sheath 4 may be flexibly bent by hooking the foremost distal end section of the sheath 4 onto the entrance of the papilla and pressing the sheath 4.

Figure 4:
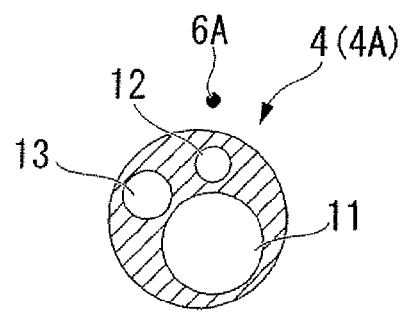
FIG. 4 is a cross-sectional view taken along a line A-A of FIG. 3.

As illustrated in FIGS. 2 to 4, three lumens 11, 12, and 13 are formed in parallel in the longitudinal directions of the sheath 4.

A first lumen having the greatest outer diameter is the guidewire lumen 11 that has an opening on the distal end thereof. The lumen 11 is used, for example, for inserting a guide wire therethrough.

A second lumen having the least outer diameter is the knife lumen 12 having a sealed distal end. Two holes 14 and 15 that open on a side of the sheath 4 at the distal end of the knife lumen 12 are formed alternately in the longitudinal direction. The conductive wire 6 is passed through the knife lumen 12. The conductive wire 6 routed through the hole 14 formed on a side of the distal end section 4A of the sheath 4 to the exterior of the sheath 4 is rerouted into the knife lumen 12 through the hole 15 formed at the distal end. The exposed portion routed to the exterior of the sheath 4 is a knife portion (hereinafter called an incision knife section 6A) for use in treatment. The distal end of the conductive wire 6 is fixed to the sheath 4 via a chip 16 embedded in the knife lumen 12. The previously described first rotation torque-transmitting section 5 does not overlap the incision knife section 6A and the hole 14 since the distal end of the first rotation torque-transmitting section 5 is disposed close to a proximate end relative to the incision knife section 6A and the hole 14. In addition, a pre-curve is imparted to the distal end section 4A of the sheath 4 in a direction that minimizes the distance between the two holes 14 and 15.

Figure 5:
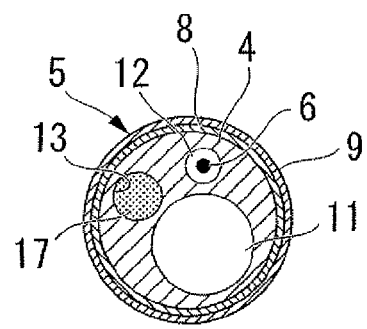
FIG. 5 is a cross-sectional view taken along a line B-B of FIG. 3.

A third lumen having the second greatest outer diameter is the liquid-feeding lumen 13 that has an opening on the distal end thereof. The liquid-feeding lumen 13 is used for supplying a contrast agent, etc. As illustrated in FIGS. 3 and 5, a second rotation torque-transmitting section that is press-fit into the distal end of the liquid-feeding lumen 13 is a rotation-transmitting core wire 17. A proximate end surface of the rotation-transmitting core wire 17 is disposed at a position that overlaps the blade 8 and the insulative tube 9. The rotation-transmitting core wire 17 extends toward the distal end from here. The distal end surface of the rotation-transmitting core wire 17 is disposed between the two holes 14 and 15 of the knife lumen 12 so that the distal end of the rotation-transmitting core wire 17 overlaps the incision knife section 6A when viewed in the longitudinal direction thereof.

The rotation-transmitting core wire 17 has a cylindrical shape, and is manufactured from a highly rotation-transmissible material such as metal. e.g., stainless-steel or NiTi. The distal end of the rotation-transmitting core wire 17 is disposed at an intermediate section of the incision knife section 6A, and more specifically, at ½ to ¾ of the distance from the distal end of the incision knife section 6A; or at 10 to 15 mm from the distal end of the incision knife section 6A. This is because an ordinary incision in many cases uses approximately ⅓ or approximately 8 mm of the knife in length measured from the tip thereof.

Figure 6:
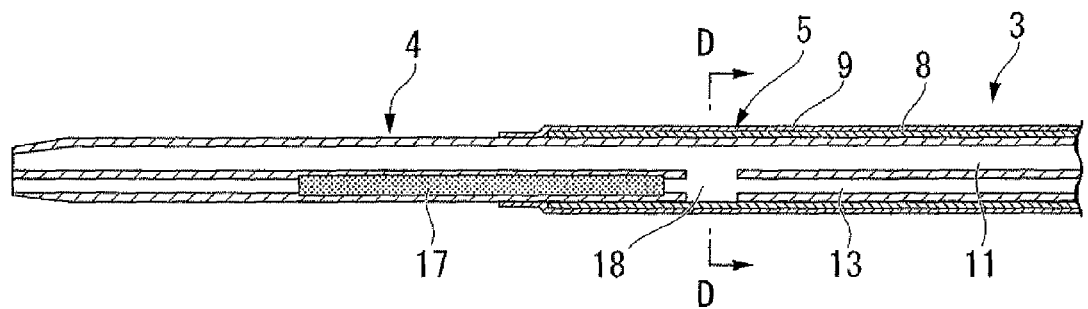
FIG. 6 is a cross-sectional view taken along a line C-C of FIG. 1.
Figure 7:
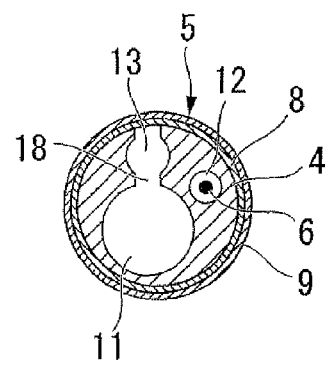
FIG. 7 is a cross-sectional view taken along a line D-D of FIG. 6.

Contrast agent, etc., cannot pass between the rotation-transmitting core wire 17 and the liquid-feeding lumen 13 because the rotation-transmitting core wire 17 is struck and fixed tightly to the liquid-feeding lumen 13 so that the rotation-transmitting core wire 17 is not capable of rotating relative to the liquid-feeding lumen 13. Accordingly, as illustrated in FIGS. 6 and 7, a communication hole 18 for communicating the liquid-feeding lumen 13 to the guidewire lumen 11 is formed on the liquid-feeding lumen 13 close to the proximate end relative to the rotation-transmitting core wire 17. A communication hole 18 is formed by drilling a hole that penetrates the guidewire lumen 11 from the outer periphery of the sheath 4 through the liquid-feeding lumen 13. An opening formed in the drilling operation on the outer periphery is blocked by the first rotation torque-transmitting section 5. Forming the communication hole 18 in this way facilitates the manufacturing of the papillotome.

As illustrated in FIG. 1, the operation section 2 has a knob 30 having the proximate end of the first rotation torque-transmitting section 5 fixed thereto. The knob 30 has a function of a first-dividing section that communicates a tube 32 to the guidewire lumen 11 in the sheath 4. The tube 32 having flexibility has an insertion section 33. A guidewire can be inserted through an end section thereof. A ring 34 is formed on a side section of the insertion section 33. The ring 34 is in a substantially C-shape having an end opening toward the distal end. Fitting the ring 34 to the endoscope causes the operation section 2 to be fixed to the endoscope. A connection section 35 unitarily extends from a side of the insertion section 33 in substantially the opposite direction in which the ring 34 extends. A recessing section 35A is formed at the distal end of the connection section 35.

In addition, the operation section 2 has an operation section's main body 36 that extends from the proximate end section of the sheath 4 beyond the knob 30. A locking section 37 is provided to the distal end of the operation section's main body 36. The locking section 37 is detachable from the recessing section 35A of the previously explained connection section 35. The operation section's main body 36 is divided into a first operation unit 39 and a second operation unit 40 via the locking section 37 and a branch section 38. The first operation unit 39 is disposed substantially coaxial with the sheath 4. A syringe is detachably attached to an end section is of the sheath 4 communicating with the liquid-feeding lumen 13. The second operation unit 40 is disposed to tilt relative to the first operation unit 39. A slider 42 freely operative in a feeding or retracting direction is attached to the second operation unit 40. A terminal 43 that can be connected to a high-frequency power supply disposed externally is attached to the slider 42. The power supply is electrically connected to the conductive wire 6 fixed to the slider 42.

A manipulation using the papillotome 1 will be explained next.

To start with, an endoscope is inserted into the mouth as a natural orifice of a patient and introduced into the duodenum. The endoscope for use may be of a side-view type that has an observation perspective lateral relative to a side of the endoscope.

Figure 8:
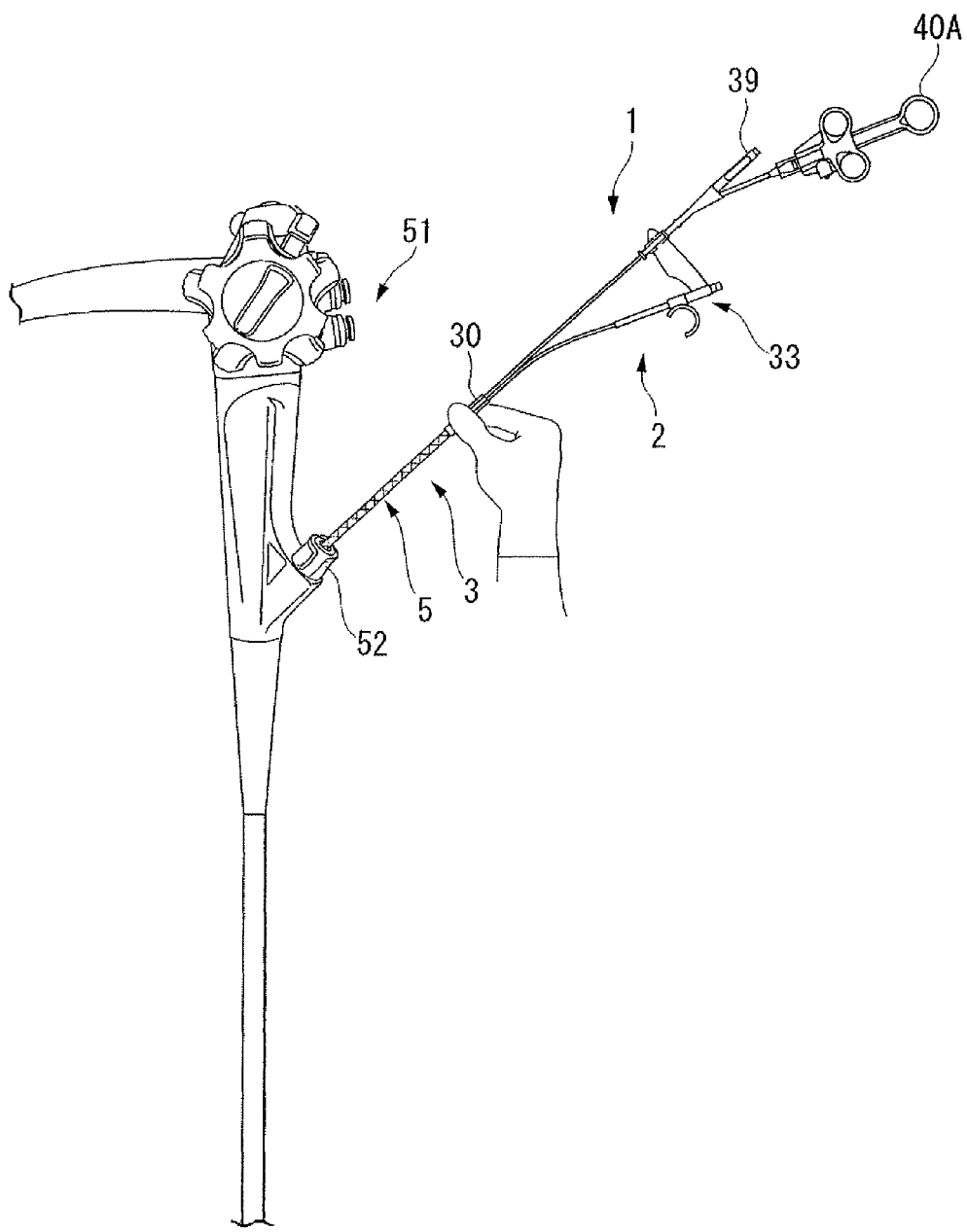
FIG. 8 is a view for explaining how to use the papillotome.
Figure 9:
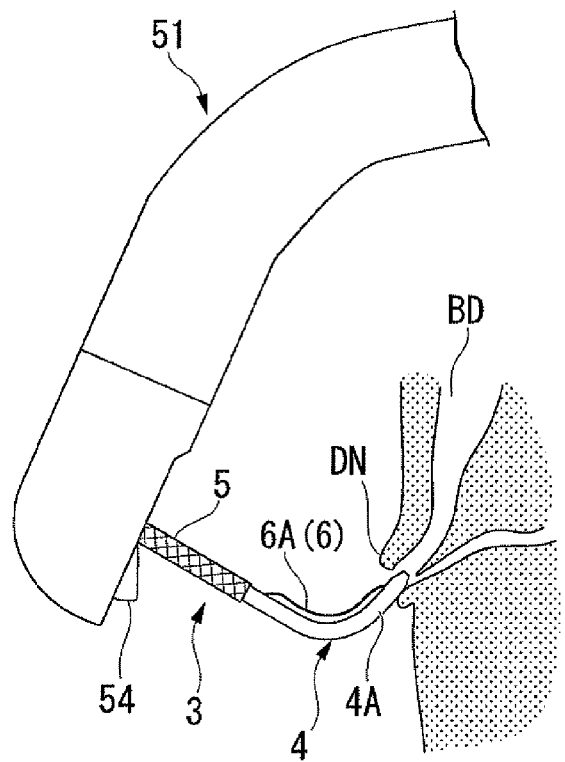
FIG. 9 shows the distal end of the papillotome directed to a bile duct.

An observation device attached to the endoscope obtains an inner-body image. The distal end section of the endoscope is guided to the vicinity of a papilla as an object to be treated. As illustrated in FIG. 8, the papillotome 1 is inserted into an operational channel via a forceps plug 52 of an endoscope 51. The distal end section 4A of the sheath 4 protrudes from the endoscope 51. As illustrated in FIG. 9, a raising block provided to the distal end of the endoscope 51 causes the papillotome 1 to protrude laterally. The distal end of the papillotome 1 directed by a pre-curve imparted onto the distal end section 4A of the sheath 4 toward a bile duct across the papilla. Alternatively the foremost distal end section of the sheath 4 is directed toward the bile duct across the papilla by compressing and hooking the foremost distal end section of the sheath 4 onto the entrance of the papilla and compressing to bend the distal end of the sheath 4 flexibly.

Figure 10:
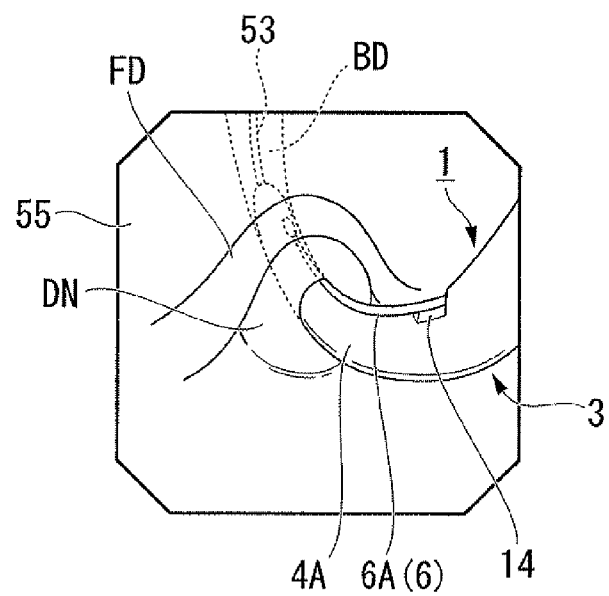
FIG. 10 is an endoscopically obtained image showing the papillotome inserted into a papilla.

As illustrated in FIG. 10, the distal end of the sheath 4 is inserted into a papilla DN when the papilla is incised. A guidewire 53 inserted into the insertion section 33 of the operation section 2 is further introduced into a bile duct BD. Although the guidewire 53 does not have to be used, the passing of the guidewire 53 through the insertion section 33 may stabilize incising of the papilla or exchanging from one treatment device to another.

A direction for incision is determined upon observing the position of an encircling fold on an endoscope image 55 (endoscopically obtained image 55). Observing the position of the bile duct BD by X-ray radiography accompanies injecting a contrast agent into the liquid-feeding lumen 13 from the syringe 41 attached to the first operation unit 39. The contrast agent passing through the liquid-feeding lumen 13 and flowing from the communication hole 18 in the vicinity of the distal end to the guidewire lumen 11 is further injected into the bile duct BD from the distal end of the guidewire lumen 11.

Figure 11:
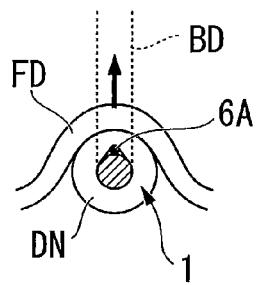
FIG. 11 illustrates dispositions of the papillotome, the papilla, and a bile duct shown in FIG. 10.

Upon determining that the direction in which an incision should be made is a twelve-o'clock direction indicated by an arrow illustrated in FIG. 11, the direction of the sheath 4 is adjusted so that the holes 14 and 15 are exposed in the twelve-o'clock direction, more specifically, the incision knife section 6A is exposed in the twelve-o'clock direction. Inserting the distal end of the distal end section 4A having a previously imparted pre-curve into the papilla DN by making use of the bending of the distal end section 4A causes the incision knife section 6A to be directed in the twelve-o'clock direction.

Figure 12:
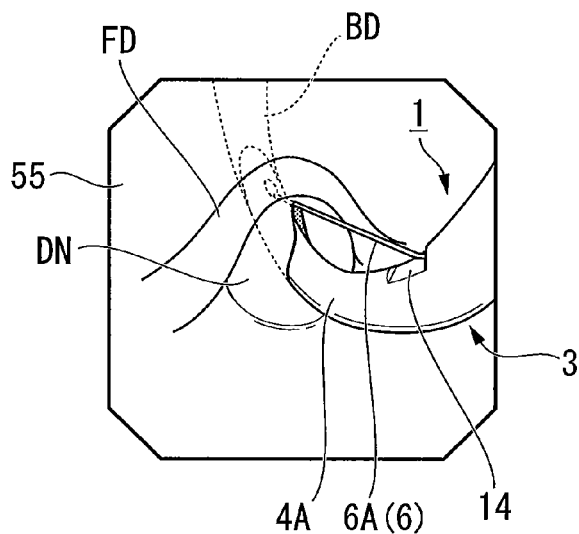
FIG. 12 illustrates a bowed state of an incision knife section that is in a beginning state of the incision to the papilla.
Figure 13:
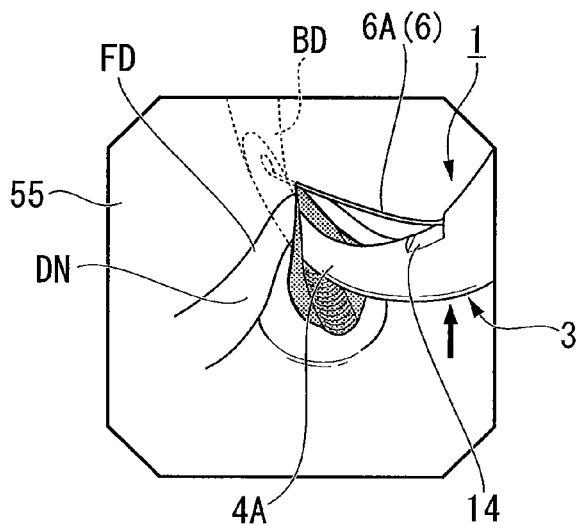
FIG. 13 illustrates the papilla that underwent a required amount of incision.

Placing fingers through the ring 40A and the slider 42 provided to the proximal end of the second operation unit 40 and retracting the slider 42 to draw the conductive wire 6 cause the distal end section 4A of the sheath 4 to bend since the distal end of the conductive wire 6 is fixed to the distal end section 4A of the sheath 4. The conductive wire 6 causes the incision knife section 6A exposed out of the sheath 4 to be stretched in a bowed state. The swinging movement of the sheath 4 is controlled by maneuvering the raising block 54 with supplying high-frequency electric current from a high-frequency power supply to the conductive wire 6 via the terminal 43 of the slider 42 of the second operation unit 40. As illustrated in FIG. 12, the tissue of the papilla DN where the incision knife section 6a is contacted is incised by applying high-frequency electric current and compressing force by the tension imparted by the incision knife section 6a. As illustrated in FIG. 13, the high-frequency electric current is stopped when a necessary incision is achieved. In addition, pushing and forwarding the slider 42 can cause dilatation of the incision knife section 6A of the conductive wire 6 outwardly in a radial direction of the sheath 4.

Figure 14:
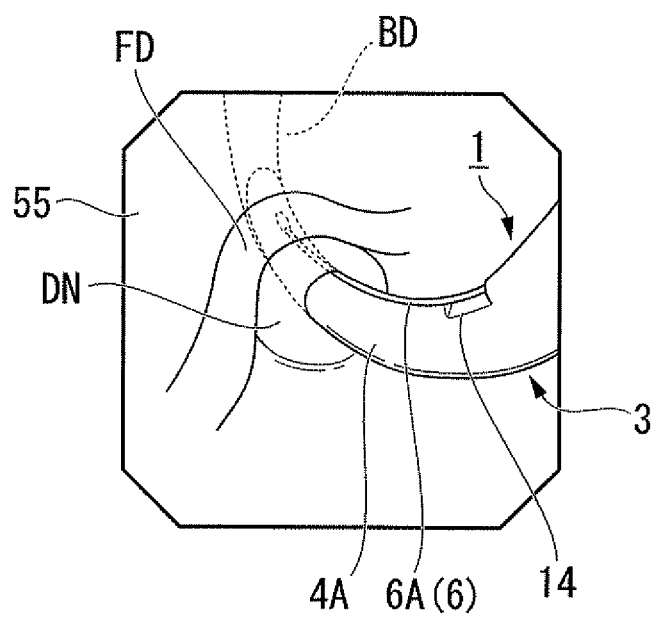
FIG. 14 illustrates an endoscopically obtained image showing a leaning state of direction in which an incision is to be carried out.
Figure 15:
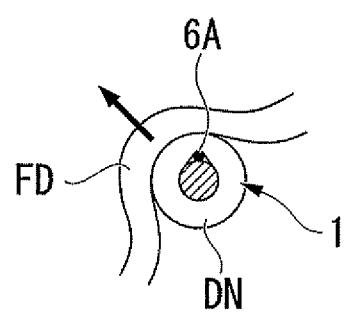
FIG. 15 illustrates dispositions of the papillotome, the papilla, and the bile duct shown in FIG. 14.

In a case as illustrated in FIGS. 14 and 15 where an observation based on an endoscope image 55 (endoscopically obtained image 55) reveals that the direction of the bile duct BD is different from the twelve-o'clock direction, more specifically, in a case where the encircling fold FD or the bile duct BD is directed in a ten-o'clock direction as indicated by an arrow shown in FIG. 15 and if it is determined to incise in this direction, an endoscopist grasps the knob 30 and rotates the knob 30 to change the direction from the twelve-o'clock direction to the ten-o'clock direction. The rotation torque transmitted to the distal end of the sheath 4 via the first rotation torque-transmitting section 5 causes the sheath 4 covered by the first rotation torque-transmitting section 5 to be rotated around the axial line thereof. The rotation torque is further transmitted to the rotation-transmitting core wire 17 which is partly disposed to overlap the first rotation torque-transmitting section 5. That is, the rotation of the proximal end section of the rotation-transmitting core wire 17 provided by means of the first rotation torque-transmitting section 5 results in rotating the entire rotation-transmitting core wire 17.

Figure 16:
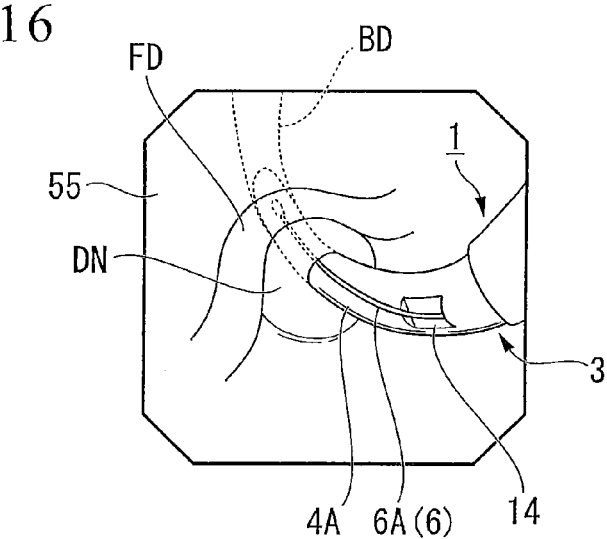
FIG. 16 illustrates a rotated state of the distal end section of a sheath by rotating a knob.
Figure 17:
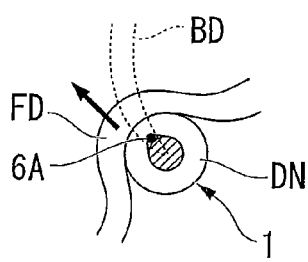
FIG. 17 illustrates dispositions of the papillotome, the papilla, and the bile duct shown in FIG. 16.
Figure 17:
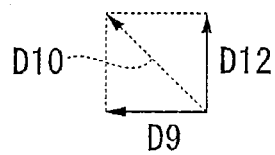

The rotation-transmitting core wire 17 is adhered and fixed tightly to the sheath 4. Therefore, the part of the sheath 4, exposed from the first rotation torque-transmitting section 5, that is adhered and fixed tightly to the rotation-transmitting core wire 17 is rotated as illustrated in FIGS. 16 and 17. The part of the sheath 4 close to the distal end relative to the rotation-transmitting core wire 17 is subsequently rotated.

This results in directing the two holes 14 and 15 and the incision knife section 6A routed therebetween in the ten-o'clock direction.

Figure 18:
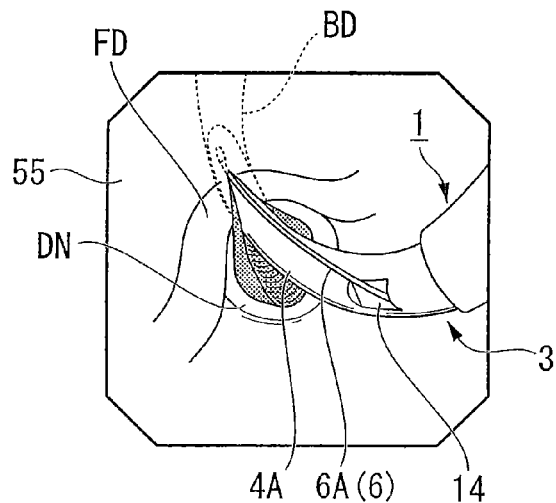
FIG. 18 illustrates the papilla by stretching a bowed state of the incision knife section from the position illustrated in FIG. 16.

High-frequency electric current is supplied to the incision knife section 6A stretched in a bowed state by the second operation unit 40. Lifting up the raising block 54 to the twelve-o'clock direction D12 while moving the distal end section of the endoscope 51 in a lateral direction, i.e., in a nine-o'clock direction D9 based on an endoscopically obtained image by twisting the insertion section or manipulation of the angulation of the endoscope 51 causes the incision knife section 6A to be moved in the ten-o'clock direction DIG. The papilla DN is incised in the ten-o'clock direction as illustrated in FIG. 18. The high-frequency electric current is stopped when a necessary incision is achieved.

The slider 42 of the second operation unit 40 is returned upon finishing the incision to the papilla DN, and then the papillotome 1 is retracted. A basket forceps instead of the papillotome 1, not shown in the drawing, is inserted along this state of the guidewire 53 remaining there. The basket forceps guided along the guidewire 53 is inserted into the bile duct BD via the incised papilla DN and grasps a calculus. A large calculus is crushed, and a small calculus is discharged without crush from the bile duct BD. The guidewire 53 is retracted upon discharging a calculus, and then the basket forceps and the endoscope 51 are retracted from the inner body.

In the present embodiment, the direction of the incision knife section 6A can be adjusted reliably in accordance with the direction of the bile duct BD since torque-transmisibility of the distal end section is enhanced by disposing the rotation-transmitting core wire 17 into the intermediate section of the incision knife section 6A and since the rotation is transmitted to the distal end of the knife.

Figure 19:
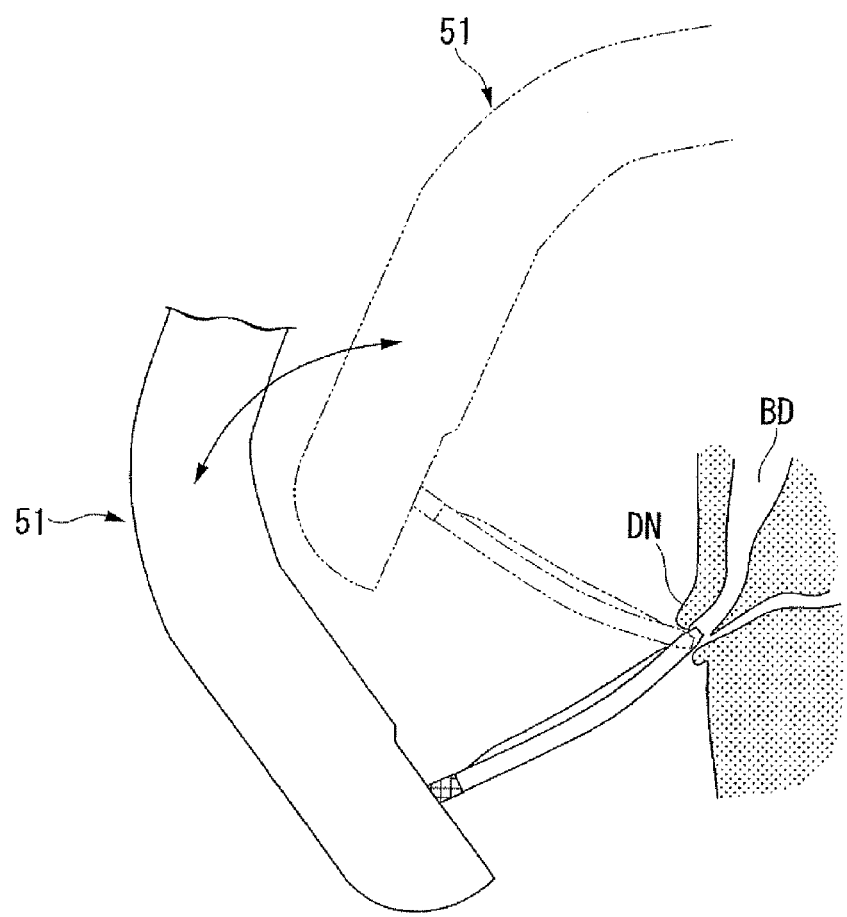
FIG. 19 explains movement required for a distal end section stiffened in a sheath in an endoscope.

Here we consider a conventional papillotome in which: a pre-curve cannot be imparted since a sheath will be stiffened when a rotation-torque-transmitting unit extends to a distal end of a knife; or the distal end of a sheath hooked and pressed onto an entrance of a papilla cannot be flexibly bent. A sheath in a non-pre-curved state or in a non-flexible state is difficult to be inserted into a bile duct BD unless the position of the sheath is significantly changed as illustrated in FIG. 19 because the sheath does not conform to the bile duct BD in angle. However, the endoscope 51 having little freedom in being moved in the duodenum could not move in that way actually. The present embodiment can facilitate aligning the angles of the sheath 4 and the bile duct BD because: a pre-curve can be imparted onto the sheath 4 close to the distal end easily; the distal end of the sheath can be hooked and compressed onto the entrance of the papilla to bend the distal end of the sheath flexibly; because the rotation-transmitting core wire 17 is disposed into the intermediate section of the incision knife section 6A. Therefore, rotatability can be enhanced without reducing insertability. With the conventional papillotome, it should be noted that, in an imaginable case where a sheath having a stretched state of the incision knife section is inserted into a papilla, the stretched state of incision knife section hinders the insertion.

Also the distal end section 4A of the sheath 4 does not buckle when the incision knife section 6A is compressed onto tissue by operating the raising block 54 and the endoscope 51 since the sheath 4 reaching a position corresponding to the intermediate section of the incision knife section 6A is stiffened by the two rotation-torque-transmitting sections 5 and 17 in the present embodiment. Therefore, an incision can be carried out more desirably since a more significant compression force can be applied to tissue to be incised while easy insertability is maintained.

A contrast agent can be injected into the bile duct through the liquid-feeding lumen 13 having the rotation-transmitting core wire 17 that is press-fit therein since the communication hole 18 is disposed for communicating the liquid-feeding lumen 13 to the guidewire lumen 11.

An example here modifying a rotation-transmitting core wire of rotation-torque-transmitting section.

Figure 20:
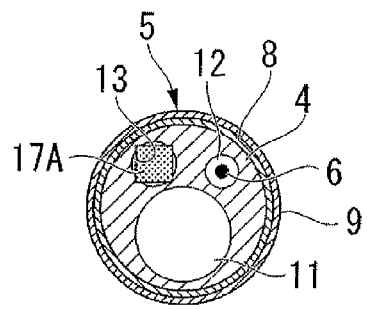
FIG. 20 illustrates a rectangular cross-section of a rotation-transmitting core wire.
Figure 21:
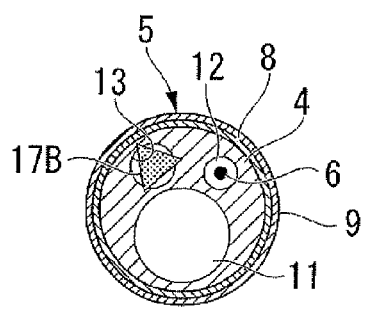
FIG. 21 illustrates a triangular cross-section of a rotation-transmitting core wire.
Figure 22:
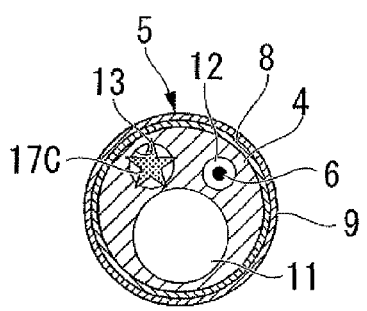
FIG. 22 illustrates a star-shaped cross-section of a rotation-transmitting core wire.

As illustrated in FIG. 20, the cross-section orthogonal to the axial line of the rotation-transmitting core wire 17A is a rectangle. As illustrated in FIG. 21, the cross-section of the rotation-transmitting core wire 17B is a triangle. As illustrated in FIG. 22, the cross-section of the rotation-transmitting core wire 17C is a star-shape. These rotation-transmitting core wires 17A to 17C are fixed to the sheath 4 more strongly by forming the cross-sections in polygonal shapes. Rotational followability is further enhanced since the rotation torque input via the first rotation torque-transmitting section 5 can be transmitted to the distal end section 4A of the sheath 4 more easily. Also forming the cross-section in polygonal shapes enables forming of spaces between the liquid-feeding lumen 13 and the rotation-transmitting core wire. In particular, a space formed between the rotation-transmitting core wire 17C and the liquid-feeding lumen 13 can be more significant because a recessing section is formed on an outer surface of the rotation-transmitting core wire 17C. Using the space enables liquid-supply without disposing the communication hole 18 (see FIG. 7).

Figure 23:
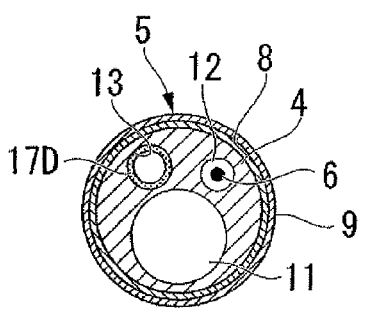
FIG. 23 illustrates a cylindrical rotation-transmitting core wire.

As illustrated in FIG. 23, the rotation-transmitting core wire 17D may be cylindrical in shape. Accordingly, the rotation torque can be transmitted and liquid-supply using an inner hole can be achieved.

It should be noted that these rotation-transmitting core wires 17 and 17A to 17D may be extended to the proximal end of the papillotome. Transmissibility of rotation torque can be enhanced. The first rotation torque-transmitting section 5 may be omitted in this case of configuration.

Second Embodiment

Figure 24:
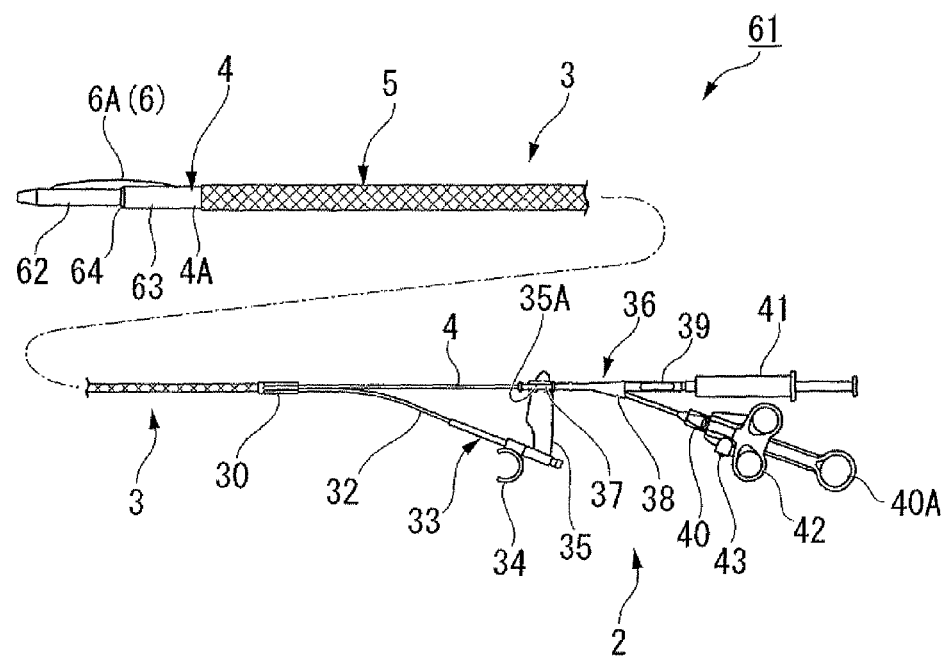
FIG. 24 is a schematic view of a papillotome having a gap section in an intermediate section of an incision knife section by varying outer diameters of the sheath.

FIG. 24 shows a configuration of a papillotome as another example of a treatment device. A papillotome 61 has a long flexible insertion section 3 extended from an operation section 2 that is operated by an endoscopist. A conductive wire 6 for use in incision is extended to a side section of an insertion section 3 relatively close to the distal end.

Figure 25:
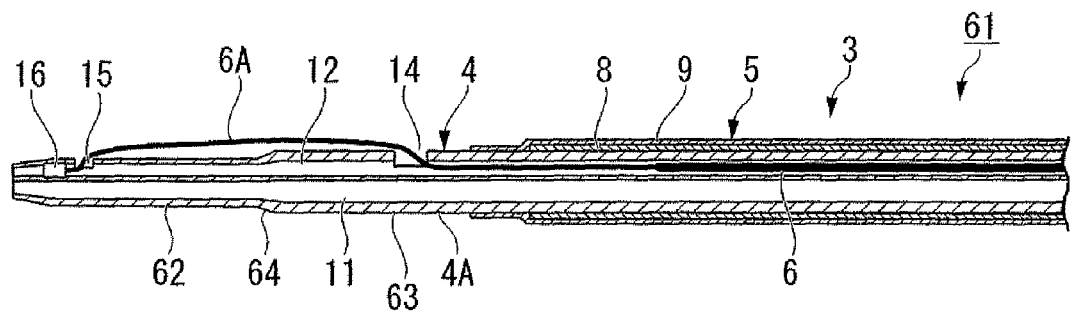
FIG. 25 is a cross-section of the distal end section of the papillotome shown in FIG. 24.

The insertion section 3 is provided with a sheath 4 and a first rotation torque-transmitting section 5. The sheath 4 has a reduced diameter section 62 and an increased diameter section 63. The outer diameter of the reduced diameter section 62 is different from the outer diameter of the increased diameter section 63 at a distal end section 4A exposed from the first rotation torque-transmitting section 5. As illustrated in FIG. 25, the reduced diameter section 62 is disposed at the distal end having a hole 15 formed thereon. The outer diameter of the increased diameter section 63 increases at a taper-shaped gap section 64 extending from the reduced diameter section 62. A hole 14 is formed on the increased diameter section 63. The outer diameter of the increased diameter section 63 is the same as an outer diameter of a part of the sheath 4 that is covered by the first rotation torque-transmitting section 5. That is, the increased diameter section 63 extending to a proximal end section overlaps the first rotation torque-transmitting section 5 at a position close to the proximal end relative to the hole 14.

The increased diameter section 63 is a second rotation torque-transmitting section having a more significant outer diameter than that of the reduced diameter section 62 and accordingly having an enhanced transmissibility for rotation torque. Increasing the thickness of the increased diameter section 63 to be greater than that of the reduced diameter section 62 further enhances the transmissibility of rotation torque. It should be noted that the thickness of the increased diameter section 63 may be the same as that of the reduced diameter section 62.

A taper-shaped gap section 64 that is a border between the reduced diameter section 62 and the increased diameter section 63 is disposed at an intermediate section of the incision knife section 6A, and more specifically, at ½ to ¾ of the distance from the distal end of the incision knife section 6A; or at 10 to 15 mm from the distal end of the incision knife section 6A. This is because an ordinary incision in many cases uses approximately ⅓ or approximately 8 mm of the knife in length measured from the tip thereof. The incision knife section 6A has a space between the incision knife section 6A and the sheath 4 since the gap section 64 is provided.

A manipulation using the papillotome 61 will be explained next.

The endoscope 51 inserted through the mouth of a patient is guided to the vicinity of a papilla DN. The papillotome 61 is passed through an operation channel and guided close to the papilla DN by using a raising block 54. The distal end of the sheath 4 is inserted into the papilla DN by using a pre-curve. A liquid-feeding lumen 13 is used for injecting a contrast agent. The contrast agent passes through the liquid-feeding lumen 13 via a syringe joined to the first operation unit 39 and is injected into a bile duct BD from a distal end surface of the sheath 4.

Figure 26:
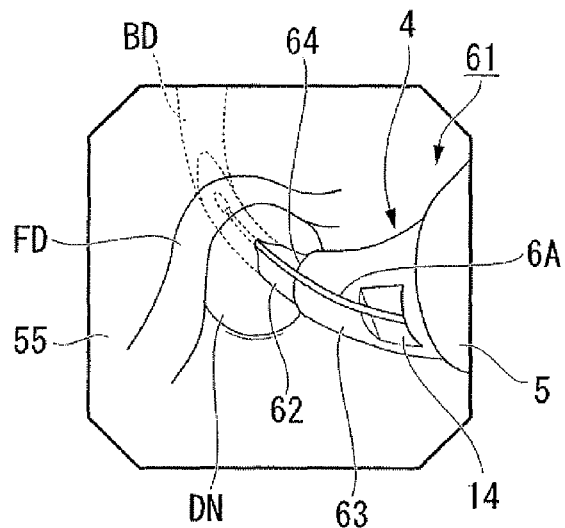
FIG. 26 illustrates an endoscopically obtained image showing the sheath rotated in accordance with the direction in which an incision is to be carried out.

High-frequency electric current is supplied to the incision knife section 6A stretched in a bowed state when the papilla DN is incised. The papillotome 61 is swung by the raising block 54 in order to incise in the twelve-o'clock direction. A knob 30 is rotated when an incision is made in a non twelve-o'clock direction, e.g., a ten-o'clock direction. Rotation torque is transmitted to the distal end section 4A by the first rotation torque-transmitting section 5. Rotation torque transmitted to the increased diameter section 63 causes the increased diameter section 63 to be rotated since the first rotation torque-transmitting section 5 overlaps the increased diameter section 63 in the axial line. The reduced diameter section 62 that is narrower and softer than the increased diameter section 63 can rotate around an axis of the sheath 4 following the rotation of the increased diameter section 63 even if the reduced diameter section 62 is in a narrow papilla DN or if the sheath 4 is bending with an acute angle along the bile duct BD. As illustrated in FIG. 26, the incision knife section 6A is directed in the ten-o'clock direction and the papilla DN is intended to incise while applying a pressure with the incision knife section 6A by moving of the distal end section 4A of the sheath 4 to the ten-o'clock direction by angle-twisting the endoscope 51 and maneuvering the raising block 54 with supplying high-frequency electric current.

Figure 27:
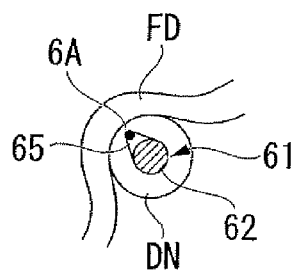
FIG. 27 illustrates dispositions of the papillotome and the papilla.
Figure 28:
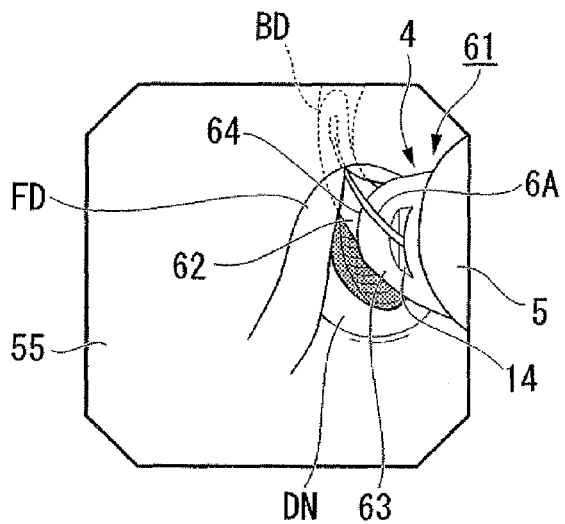
FIG. 28 illustrates a papilla incised with a non-bowed state of the incision knife section.

This state of the papillotome 61 can incise the papilla DN without stretching the incision knife section 6A in a bowed state. Since a wire 6 constituting the incision knife section 6A has an appropriate hardness, a space is formed between a part of the wire 6 that bridges over the gap section 64 and the sheath 4. That is, a space 65 is achieved between the sheath 4 (reduced diameter section 62) and the incision knife section 6A even if these are inserted into the papilla DN as illustrated in FIG. 27. Inserting a part of the gap section 64 of the incision knife section 6A slightly close to the distal end into a position that is to be incised and operating the endoscope 51 and the raising block 54 to compress the sheath 4 in the ten-o'clock direction cause the incision knife section 6A alone to be compressed to tissue with separating from the sheath 4. Therefore, a pressure necessary for incision can be applied between the incision knife section 6A and the tissue of the papilla DN. Also heat for incision can be prevented from being transferred to the sheath 4. This results in proceeding of incision as illustrated in FIG. 28 without being affected by the sheath 4. Even if the gap section 64 is small, as long as the gap section 64 can make a certain distance between the conductive wire 6 and the sheath 4, this is effective for preventing the pressure or heat from being transferred therefrom.

The present embodiment enhances torque transmissibility by increasing the outer diameter of sheath reaching the intermediate section of the incision knife section 6A. Since the narrow and flexible distal end of the sheath 4 can be easily rotated around the axis of the sheath 4 even if the distal end is disposed in a narrow hollow organ or bent in a acute angle along the bile duct, rotation can be transmitted to the distal end of the knife and the direction of the incision knife section 6A can be adjusted in accordance with the direction of the bile duct BD.

Figure 29:
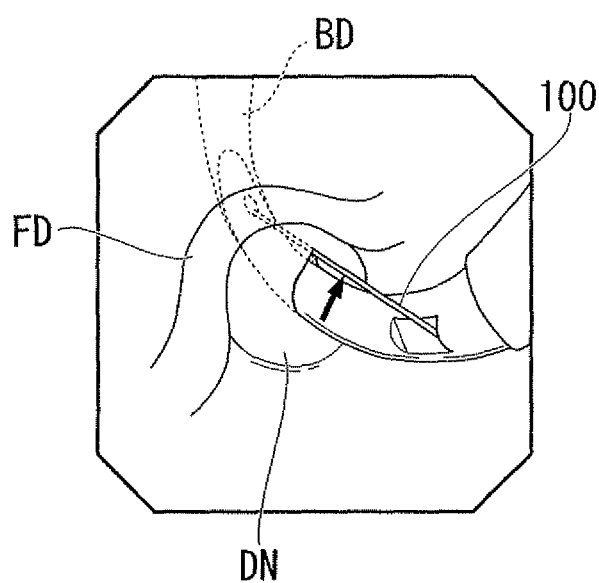
FIG. 29 illustrates a maneuvering of a conventional papillotome which is directed in the twelve-o'clock direction when a knife is stretched in a bowed state.
Figure 30:
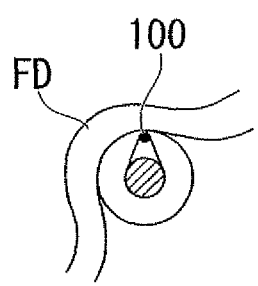
FIG. 30 illustrates dispositions of the papillotome, the papilla, and the bile duct shown in FIG. 29 showing a direction in which an incision is carried out that does not coincide with the direction of a knife for use in incision.

The sheath 4 that is curved between the papilla and the distal end of the endoscope may sometimes have to encounter intensive acuteness that depends on the correlation between the papilla and the endoscope. In such a case of a conventional papillotome, the incision knife section 100 may sometimes move in the ten-o'clock direction as shown in FIGS. 29 and 30, when the incision knife section 100 is stretched in a bowed state by pulling a slider to pull a conductive wire, even if the incision knife section 100 is rotated and directed in the ten-o'clock direction. Although incision must be conducted with a knife as loose as possible in such a case, significant pressure cannot be applied to the knife due to there being little space between the sheath and the knife, therefore incision is difficult.

However, according to the present embodiment a non-bowed state of the incision knife section 6A can apply pressure to tissue and thus desirable incision can be achieved since the incision knife section 6A is routed over the gap section 64 of the sheath 4.

It should be noted that, since the opening of the papilla DN is extremely narrow, the sheath having a significant diameter reaching to the distal end of the knife is difficult to insert into the papilla DN. Furthermore, insertion is difficult since a pre-curve is hardly imparted to this case of a stiffened sheath or the distal end of the sheath is difficult to hook and compress onto the entrance of the papilla to be flexibly bent. In contrast, the papillotome 61 has desirable insertability and rotatability since the sheath 4 reaching the intermediate section of the incision knife section 6A is increased in diameter; the distal end therefrom is narrowed and softened; pre-curve is easily imparted; or the distal end of the sheath 4 can be easily hooked onto the papilla to be flexibly bent. Changing the diameter of the sheath 4 alone can achieve cost reduction without increasing the number of parts.

Since the sheath 4 reaching a position corresponding to the intermediate section of the incision knife section 6A is increased in diameter, significant pressure can be applied to tissue while preventing the sheath 4 from buckling in a case where the incision knife section 6A is compressed to the tissue by operating the raising block 54 and the endoscope 51.

Third Embodiment

Figure 31:
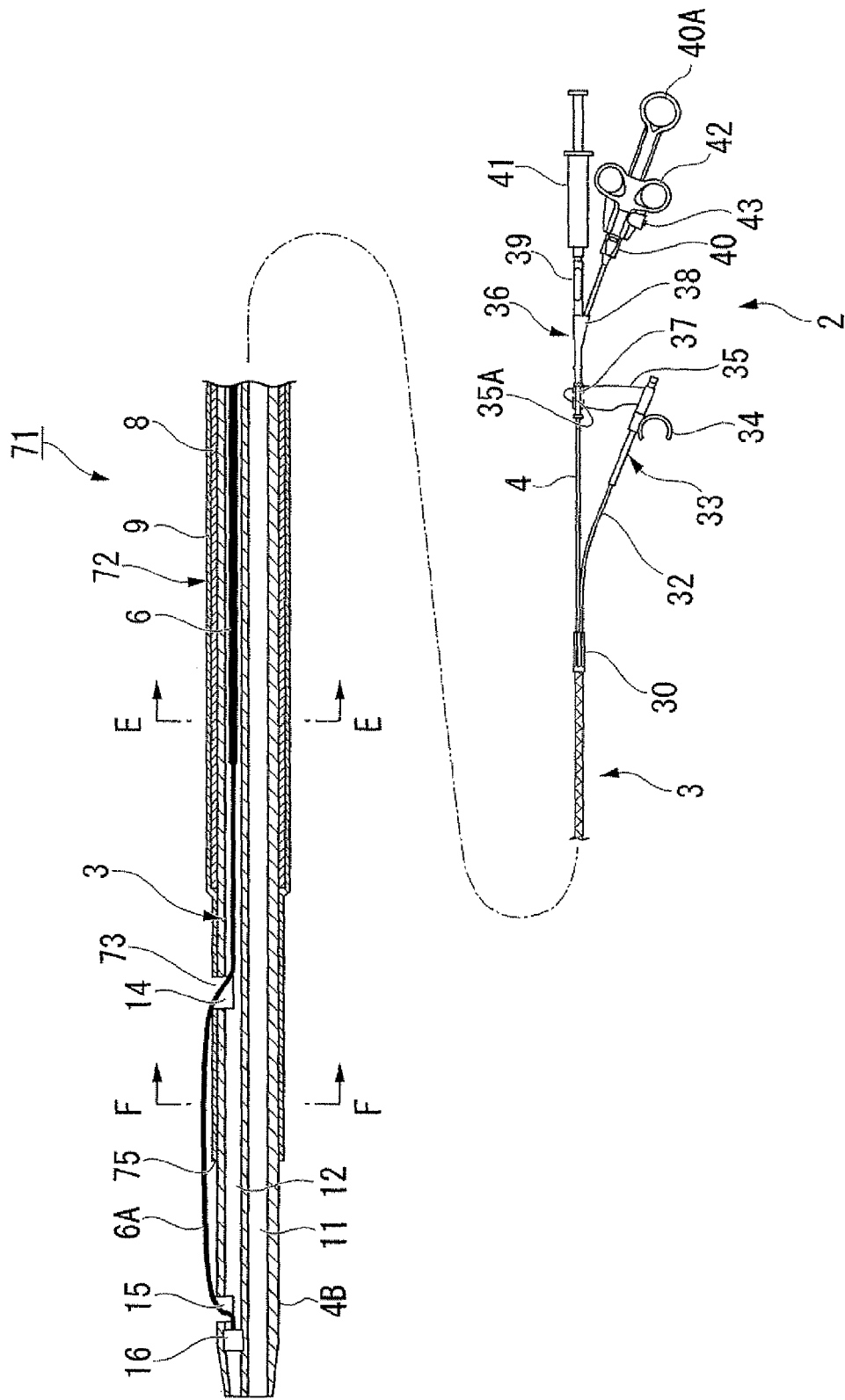
FIG. 31 illustrates a cover tube in a rotation-torque-transmitting section extending to an intermediate section of an incision knife section.

FIG. 31 shows a configuration of a papillotome as another example of a treatment device. A papillotome 71 has a long flexible insertion section 3 extended from an operation section 2 that is operated by an endoscopist. A conductive wire 6 for use in incision is extended to a side section of an insertion section 3 close to the distal end.

Figure 32:
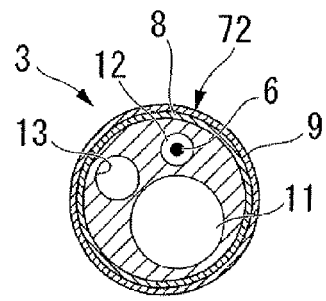
FIG. 32 is a cross-sectional view taken along a line E-E of FIG. 31.
Figure 33:
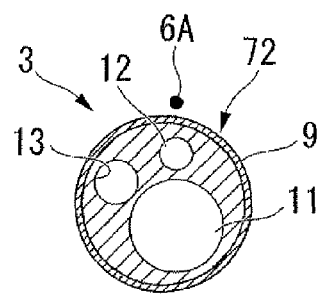
FIG. 33 is a sectional view taken along a line F-F in FIG. 31.

The insertion section 3 has a sheath 4. A rotation-torque-transmitting section 72 covers the outer periphery of the sheath 4 except for a part of the distal end. The rotation-torque-transmitting section 72 is formed of a metal-made blade 8 attached onto the sheath 4 that is further covered by an insulative tube 9. The proximal end of the rotation-torque-transmitting section 72 is fixed to a knob 30. As illustrated in FIGS. 31 and 32, the blade 8 extends slightly in the vicinity of the hole 14. As illustrated in FIGS. 31 and 33, the insulative tube 9 extends to an intermediate section of an incision knife section 6A across the hole 14. More specifically, the distal end of the insulative tube 9 is disposed at ½ to ¾ of the distance from the distal end of the incision knife section 6A; or at 10 to 15 mm from the distal end of the incision knife section 6A. An opening section 73 is formed on the insulative tube 9 corresponding to the position of the hole 14. A conductive wire 6 extracted through the opening section 73 forms the incision knife section 6A. A gap section 75 is formed between the distal end of the insulative tube 9 and the sheath 4. The incision knife section 6A has a space between the incision knife section 6A and the sheath 4 since the gap section 75 is provided. A part of the insertion section 3 covered by the rotation-torque-transmitting section 72 is stiffened more strongly than the distal end section 4B from which the sheath 4 is exposed.

A manipulation using the papillotome 71 will be explained next.

The papillotome 71 is passed through an endoscope 51 and guided close to the papilla DN by using a raising block 54. The distal end of the sheath 4 is inserted into the papilla DN by using a pre-curve, and the papilla DN is incised by the incision knife section 6A. A liquid-feeding lumen 13 is used for injecting a contrast agent. The contrast agent passing through the liquid-feeding lumen 13 is injected into the bile duct BD from the distal end.

The knob 30 is rotated when the direction of incision is adjusted. Rotation torque is transmitted to the distal end by the rotation-torque-transmitting section 72. A distal end section 4B of the sheath 4 rotates while following the rotation of the covered part. When the distal end section 4B of the sheath 4 is moved to a direction of incision, e.g., a ten-o'clock direction, the distal end section 43 of the sheath 4 is moved to the ten-o'clock direction, and the papilla DN is incised while applying pressure to the papilla DN with the incision knife section 6A that is supplied with high-frequency electric current.

Figure 34:
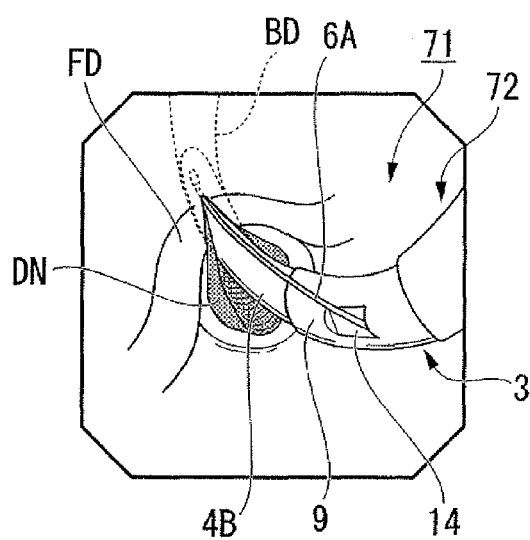
FIG. 34 illustrates a papilla incised with a bowed state of an incision knife section.

As illustrated in FIG. 34, the papilla DN can be incised by stretching the incision knife section 6A in a bowed state. Alternatively the papilla DN may be incised with a non-bowed state of the incision knife section 6A. Either way of incision movements are the same as those of the second embodiment.

In the present embodiment, the direction of the incision knife section 6A can be adjusted in accordance with the direction of the bile duct BD since torque-transmissibility is enhanced by covering the intermediate section of the incision knife section 6A of the sheath 4 by the insulative tube 9 and since the rotation is transmitted to the distal end of the knife.

Other effects are the same as those in the second embodiment. In addition, further cost reduction can be achieved than in the second embodiment since time and manpower for forming the gap section 64 by narrowing the sheath 4 can be omitted in the present embodiment.

Fourth Embodiment

Figure 35:
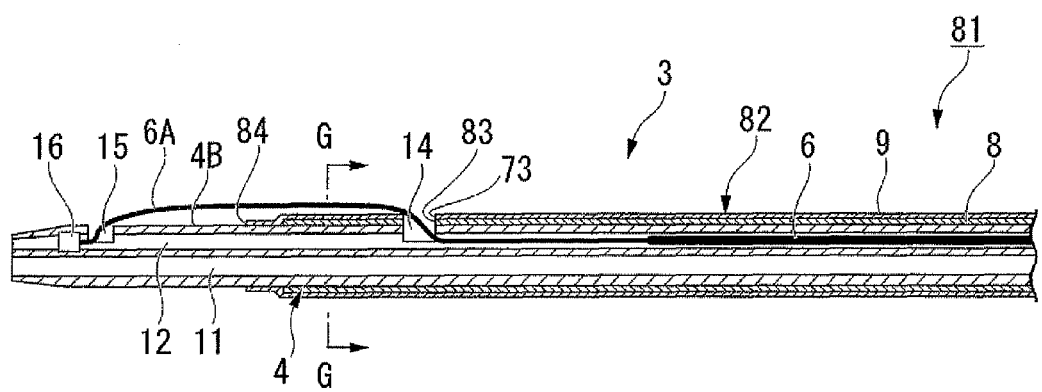
FIG. 35 illustrates the cover tube and a blade in the rotation-torque-transmitting section extending to the intermediate section of the incision knife section.
Figure 36:
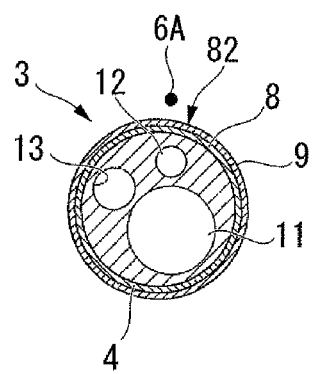
FIG. 36 is a sectional view taken along a line G-G in FIG. 35.

FIGS. 35 and 36 show a configuration of a papillotome as another example of a treatment device. The papillotome 81 is provided with a rotation-torque-transmitting section 82 that mainly covers the proximal end of the sheath 4. The blade 8 and the insulative tube 9 both extend beyond the hole 14 to the intermediate section of the incision knife section 6A. Therefore, the blade 8 and the insulative tube 9 each has an opening section 83 and an opening section 73 that are formed in accordance with the position of the hole 14. The position of the distal end of the rotation-torque-transmitting section 82 and other configuration are the same as those in the third embodiment. A space is provided between the incision knife section 6A and the distal end section 4B of the sheath 4. The space is formed by a gap section 84 that is formed by the distal end of the rotation-torque-transmitting section 82. The proximal end of the rotation-torque-transmitting section 82 is fixed to the knob 30.

Movement and effect achieved by the papillotome 81 are the same as those in the third embodiment. Further desirable transmissibility of rotation torque can be achieved than that in the third embodiment because the blade 8 extends to the intermediate section of the incision knife section 6A.

Fifth Embodiment

Figure 37:
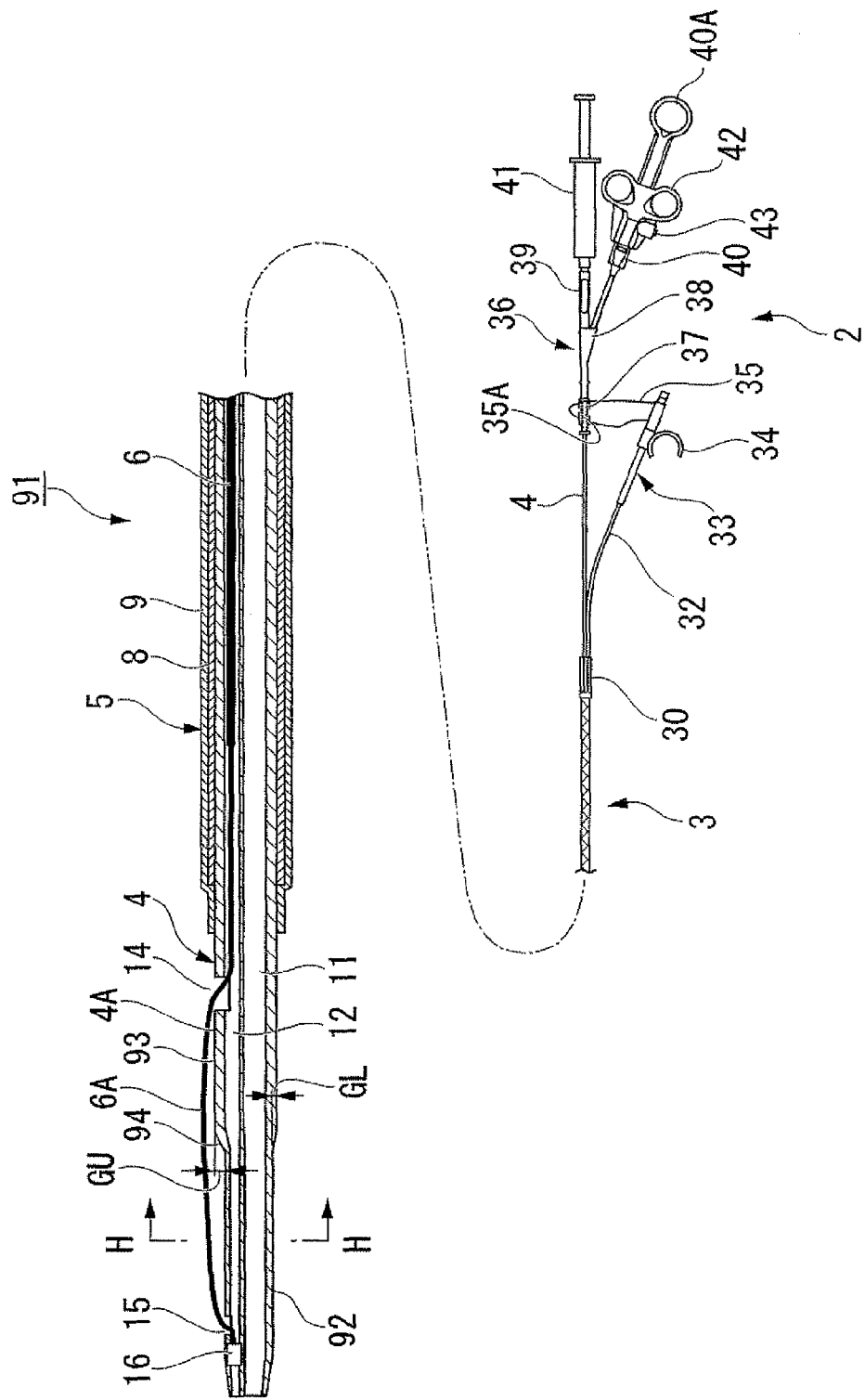
FIG. 37 illustrates a gap section formed by disposing a sheath eccentrically.
Figure 38:
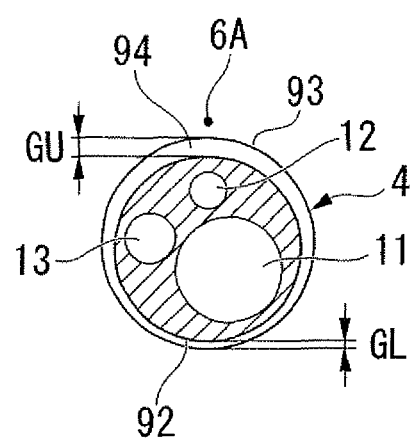
FIG. 38 is a cross-sectional view taken along a line H-H of FIG. 37.

FIG. 37 shows a configuration of a papillotome as another example of a treatment device. The insertion section 3 of a papillotome 91 is provided with a sheath 4 and a first rotation torque-transmitting section 5. A first rotation torque-transmitting section 5 extends from the knob 30 to the vicinity of the hole 14A and a reduced diameter section 92 and an increased diameter section 93 of the sheath 4 are formed by disposing the distal end section 4A exposed from the first rotation torque-transmitting section 5 eccentrically at a border of the intermediate section of the incision knife section 6A.

The reduced diameter section 92 having a narrower diameter than other portions is disposed at the distal end. The increased diameter section 93 having a relatively increased diameter and a more significant hardness than the reduced diameter section 92 becomes a second rotation torque-transmitting section. The increased diameter section 93 is the same as a part of the sheath 4 that is covered by the first rotation torque-transmitting section 5. That is, the increased diameter section 93 extending to a proximal end section overlaps the first rotation torque-transmitting section 5 at a position close to the proximal end relative to the hole 14.

Furthermore, the border of the increased diameter section 93 and the reduced diameter section 92 is a taper-shaped gap section 94.

The gap section 94 is positioned at ½ to ¾ of the distance from the distal end of the incision knife section 6A; or at 10 to 15 mm from the distal end of the incision knife section 6A. The direction of the eccentric axial line of the reduced diameter section 92 relative to the axial line of the increased diameter section 93 is indicated by a direction in which the axial line of the reduced diameter section 92 separates from the knife lumen 12 on diameter of the sheath 4 that passes through the knife lumen 12. Therefore, the end of the gap section 64 directed toward the knife lumen 12 is significant in size, and the opposite end is less significant in size. A gap GU formed by the gap section 94 disposed at the knife lumen 12 has the same size as that of the second embodiment. A gap GL formed by the gap section 94 disposed at the opposite end is substantially 0 (zero).

Movement and effects achieved by the papillotome 91 during incision are the same as those in the second embodiment.

The outer diameter of the reduced diameter section 92 is 1.7 to 1.9 mm in a case in which the papillotome is provided with a guidewire lumen 11 having a size that allows a guidewire having 0.035 inch (0.89 mm) to be inserted therethrough; and a liquid-feeding lumen 13 that facilitates contrast agent injection. In contrast, the diameter of the increased diameter section 93 is limited by disposition of the first rotation torque-transmitting section 5, insertability of the endoscope 51 into an operation channel, or ease of lifting-up movement by the raising block 54. Therefore the gap section 94 at the incision knife section 6A required for incision can be maximized in the limited dimensions by forming the gap GU formed by the gap section 94 at the incision knife section 6A more significantly in size than the gap CL disposed at the opposite end. Also, the opposite end of the incision knife section 6A rubs against the raising block 54 during extension or retraction of the sheath 4. If a gap in this section is less significant or zero, the sheath 4 can be extended or retracted smoothly, thus the operation for inserting the papillotome 91 into a papilla can be facilitated.

It should be noted that a gap section may be formed by shaving the distal end section of the sheath 4.

Although the present invention has been described with respect to its preferred embodiments, the present invention is not limited to the embodiments described above. The configuration of the present invention allows for addition, omission, substitution and further replacement without departing from the spirit and scope of the present invention. The present invention is not limited to the above descriptions but is limited only by the appended claims.

What is claimed is:

1. A treatment device comprising:
    a sheath elongated in a longitudinal direction, the sheath having flexibility and being configured to be passed through an endoscope and to be introduced to an object to be treated, the sheath further having a first internal lumen extending in the longitudinal direction and a second internal lumen extending in the longitudinal direction parallel to the first internal lumen;
    a conductive wire having a first portion disposed in the first internal lumen and a second portion forming an incision knife, the incision knife being disposed in the longitudinal direction of the sheath around an outer periphery of the sheath, the incision knife being configured for incising tissue of the object to be treated; and
    a rotation-torque-transmitting member configured for rotating the sheath by transmitting rotation torque input by a user at the proximal end side of the sheath, wherein the rotation-torque-transmitting member comprises:
        a first rotation-torque-transmitting section having a distal end and being attached on an outer periphery of the sheath; and
        a second rotation-torque-transmitting section at least partially disposed in the second internal lumen and extending in the longitudinal direction of the sheath, the second rotation-torque-transmitting section having:
            a distal end positioned between a distal end of the sheath and the distal end of the first rotation-torque-transmitting section; and
            a proximal end positioned proximally to the distal end of the first rotation-torque-transmitting section.

2. The treatment device according to claim 1, wherein the first rotation-torque-transmitting section comprises a blade having a tubular shape and made of a metal which is attached to the sheath so as to cover a whole circumference of the outer periphery of the sheath and an insulative tube covering the blade.

3. The treatment device according to claim 2, wherein a distal end of the insulative tube is disposed between the distal and proximal ends of the incision knife.

4. The treatment device according to claim 1, wherein the incision knife is offset in a radial direction from a central axis of the first rotation-torque-transmitting section.

5. The treatment device according to claim 1, wherein the sheath includes a reduced diameter section formed at a position between the distal and proximal ends of the incision knife and distally to the distal end of the first rotation-torque-transmitting section, the reduced diameter section having a smaller external diameter than that of proximal portions of the sheath.

6. The treatment device according to claim 1, wherein the second rotation-torque-transmitting section is entirely disposed in the second internal lumen of the sheath.

7. The treatment device according to claim 6, wherein the second rotation-torque-transmitting section occludes transmission of a fluid through the second internal lumen of the sheath.

8. The treatment device according to claim 7, wherein a passageway is formed between the first and second internal lumens at a position proximal to the proximal end of the second rotation-torque-transmitting section to permit fluid flow from the second internal lumen to the second internal lumen.

9. The treatment device according to claim 6, wherein the second rotation-torque-transmitting section having a cross-sectional shape which permits transmission of a fluid through the second internal lumen of the sheath.

10. The treatment device according to claim 9, wherein the cross-section shape is such that the fluid is transmitted between an outer surface of the second rotation-torque-transmitting section and an inner surface of the second internal lumen.

11. The treatment device according to claim 9, wherein the cross-section shape is such that the fluid is transmitted through an internal lumen in the second rotation-torque-transmitting section.

12. The treatment device according to claim 1, wherein the distal end of the first rotation-torque-transmitting section is positioned proximally to the proximal end of the incision knife.

13. The treatment device according to claim 1, wherein the distal end of the first rotation-torque-transmitting section is positioned between the distal and proximal ends of the incision knife.

* * * * *